(12) United States Patent
Jafari

(10) Patent No.: US 11,541,253 B2
(45) Date of Patent: Jan. 3, 2023

(54) DEVICE AND METHOD FOR MEASURING RADIATION DOSAGE

(71) Applicant: TrueInvivo Limited, Surrey (GB)

(72) Inventor: Shakardokht Jafari, Surrey (GB)

(73) Assignee: TrueInvivo Limited, Surrey (GB)

( * ) Notice: Subject to any disclaimer, the term of this patent is extended or adjusted under 35 U.S.C. 154(b) by 166 days.

(21) Appl. No.: 16/966,746

(22) PCT Filed: Jan. 31, 2019

(86) PCT No.: PCT/GB2019/050278
§ 371 (c)(1),
(2) Date: Jul. 31, 2020

(87) PCT Pub. No.: WO2019/150126
PCT Pub. Date: Aug. 8, 2019

(65) Prior Publication Data
US 2020/0360732 A1    Nov. 19, 2020

(30) Foreign Application Priority Data

Feb. 2, 2018  (GB) ..................... 1801730

(51) Int. Cl.
*A61N 5/10*    (2006.01)
*A61B 1/31*    (2006.01)
(Continued)

(52) U.S. Cl.
CPC .............. *A61N 5/1071* (2013.01); *A61B 1/31* (2013.01); *A61M 25/10* (2013.01); *G01T 1/11* (2013.01)

(58) Field of Classification Search
CPC ........ A61M 25/10; A61B 1/31; A61N 5/1071; G01T 1/02; G01T 1/06; G01T 1/10; G01T 1/11
See application file for complete search history.

(56) References Cited

U.S. PATENT DOCUMENTS 3,100,262 A * 8/1963 Shenker ............... G01T 1/10
                                             250/484.5
5,066,863 A * 11/1991 Hanisch ............... G01T 1/06
                                             250/474.1
(Continued)

FOREIGN PATENT DOCUMENTS

KR    20090013894 A    2/2009
WO    2010/080905 A2    7/2010
(Continued)

OTHER PUBLICATIONS

UKIPO Search Report for GB1801730.1 dated Aug. 3, 2018.
(Continued)

*Primary Examiner* — Samuel G Gilbert
(74) *Attorney, Agent, or Firm* — Chang & Hale LLP

(57) ABSTRACT

A device for measuring radiation dosage is disclosed, comprising a flexible sheet, one or more detector assemblies disposed on the sheet, and detector retaining means for retaining the one or more detector assemblies on the sheet such that the one or more detector assemblies adopt the same curvature as the sheet when the sheet is deformed. Each one or more detector assembly comprises a plurality of beads threaded onto a fibre, the plurality of beads comprising radiation-sensitive material for recording information about a radiation dosage to which each bead is exposed, and the detector retaining means is configured to permit each one or more detector assembly to be subsequently detached from the sheet without removing the plurality of beads from the fibre. A method of detecting radiation dosage using the device is also disclosed.

20 Claims, 4 Drawing Sheets

(51) Int. Cl.
*A61M 25/10* (2013.01)
*G01T 1/11* (2006.01)

(56) References Cited

U.S. PATENT DOCUMENTS

| | | |
|---|---|---|
| 2005/0031082 A1 | 2/2005 | Haaga et al. |
| 2010/0127181 A1 | 5/2010 | Lovoi et al. |
| 2015/0346350 A1* | 12/2015 | Ziegler ................ H01L 31/085 |
| | | 250/370.07 |

FOREIGN PATENT DOCUMENTS

| | | |
|---|---|---|
| WO | 2010/118478 A1 | 10/2010 |
| WO | 2015/182853 A1 | 12/2015 |
| WO | 2016/171388 A1 | 10/2016 |
| WO | 2017/033029 A1 | 3/2017 |

OTHER PUBLICATIONS

International Search Report and Written Opinion for PCT/GB2019/050278 dated May 7, 2019.

Examination Report for Indian Application No. 202047037069 dated Apr. 28, 2022.

* cited by examiner

DEVICE AND METHOD FOR MEASURING RADIATION DOSAGE

TECHNICAL FIELD

The present invention relates to a device and method for measuring radiation dosage.

BACKGROUND

Radiation dosimeters have been developed which comprise glass beads strung onto a thread. When a bead is exposed to radiation, an electron in a low energy state absorbs energy from an incident photon and transitions to a higher energy state. As a result, the electron is excited and become trapped in a high energy state. The number of excited electrons is proportional to the radiation dose. The radiation dosage received by the bead can subsequently be determined by various methods, for example by heating the bead to trigger thermo-luminescence, such that the energy of the emitted photons provides a measure of the radiation dose to which the bead was exposed. However, such dosimeters can only provide a measure of radiation dosage along the axis of the thread.

The invention is made in this context.

SUMMARY OF THE INVENTION

According to a first aspect of the present invention, there is provided a device for measuring radiation dosage, the device comprising a sheet, one or more detector assemblies disposed on the sheet, each one or more detector assembly comprising a plurality of beads threaded onto a fibre, the plurality of beads comprising radiation-sensitive material for recording information about a radiation dosage to which each bead is exposed, and detector retaining means for retaining the one or more detector assemblies on the sheet, the detector retaining means being configured to permit each one or more detector assembly to be subsequently detached from the sheet without removing the plurality of beads from the fibre.

In some embodiments according to the first aspect, the sheet is configured to be flexible and the plurality of beads of the one or more detector assemblies are distributed across a two-dimensional area of the sheet, such that when the sheet is deformed the plurality of beads provide a plurality of radiation measurement points within a three-dimensional volume.

In some embodiments according to the first aspect, at least one of the one or more detector assemblies includes one or more marker beads among the plurality of beads, the one or more marker beads being configured to be distinguishable from other ones of the plurality of beads in an image of the device.

In some embodiments according to the first aspect, the one or more marker beads are configured to be distinguishable from other ones of the plurality of beads in one or more of a Magnetic Resonance Imaging MRI image, an ultrasound image, an x-ray image, or a Computerised Tomography CT image.

In some embodiments according to the first aspect, the one or more marker beads are formed of different material to the other ones of the plurality of beads so as to provide contrast with said other ones of the plurality of beads in the image.

In some embodiments according to the first aspect, the one or more marker beads have a different shape and/or size to said other ones of the plurality of beads.

In some embodiments according to the first aspect, the one or more marker beads comprise a cluster of beads with a different spacing between beads along the fibre, relative to a spacing between said other ones of the plurality of beads along the fibre.

In some embodiments according to the first aspect, the sheet comprises a biocompatible material.

In some embodiments according to the first aspect, the detector retaining means is configured to retain the one or more detector assemblies on the sheet when the device is positioned in or on a human or animal body.

In some embodiments according to the first aspect, the sheet forms a wall of an inflatable balloon, the balloon comprising a fluid inlet adapted for connection to a source of fluid for inflating the balloon.

In some embodiments according to the first aspect, the detector retaining means comprises a second layer of sheet material disposed around the one or more detector assemblies and the balloon, the second layer of sheet material extending around a circumference of the balloon and being sized such that the one or more detector assemblies are tightly held between the second layer of sheet material and the wall of the balloon when the balloon is inflated. The second layer of sheet material may be in the form of a second balloon.

In some embodiments according to the first aspect, the balloon is adapted for insertion into a body cavity or organ of a human or animal body. For example, the body cavity may be a rectal, oral or vaginal cavity, or wherein the organ is a bladder.

In some embodiments according to the first aspect, the sheet comprises an open mesh. The detector retaining means may, for example, comprise fibres integral to the mesh, the one or more detector assemblies being woven between said fibres.

In some embodiments according to the first aspect, the sheet comprises a part or whole of a wearable item.

According to a second aspect of the present invention, there is provided a method of detecting radiation dosage using a device according to the first aspect, the method comprising positioning the device at a location to be exposed to radiation, exposing the device to radiation, capturing an image of the device at said location, before, during or after the device is exposed to the radiation, detaching one of the one or more detector assemblies from the sheet, loading said detector assembly into a reader for reading a radiation dosage recorded by each of the plurality of beads, and determining a radiation dosage at a point in space based on the radiation dosage read from one of the plurality of beads and a position of said one of the plurality of beads in the captured image.

BRIEF DESCRIPTION OF THE DRAWINGS

Embodiments of the present invention will now be described, by way of example only, with reference to the accompanying drawings, in which.

DETAILED DESCRIPTION

Figure 1:
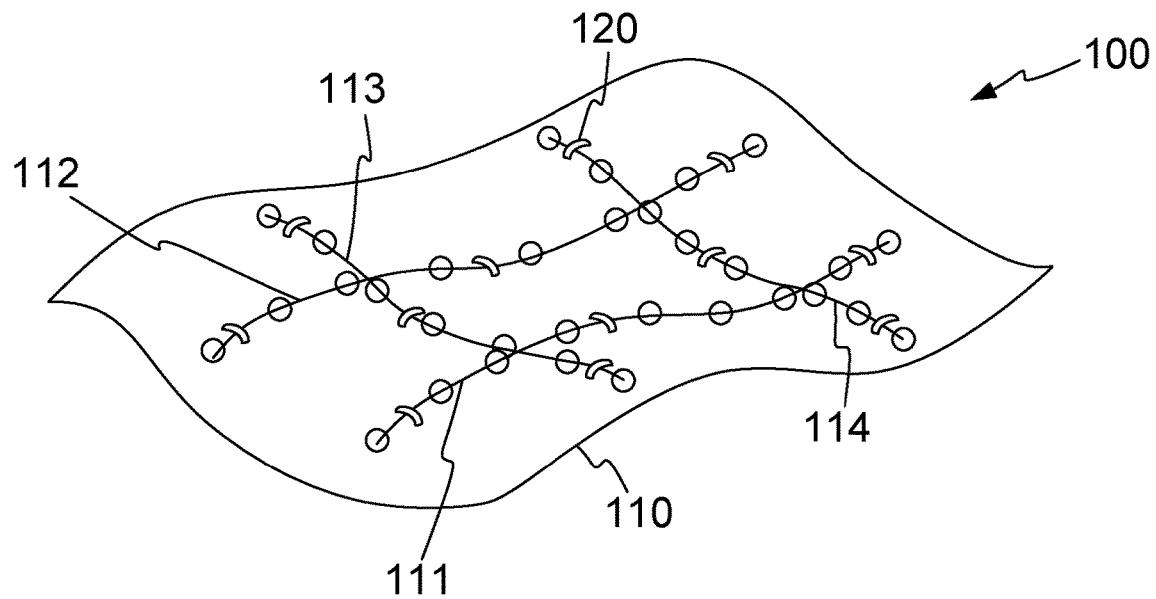
FIG. 1 illustrates a device for measuring radiation dosage according to an embodiment of the present invention.

In the following detailed description, only certain exemplary embodiments of the present invention have been shown and described, simply by way of illustration. As those skilled in the art would realise, the described embodiments may be modified in various different ways, all without departing from the scope of the present invention. Accordingly, the drawings and description are to be regarded as illustrative in nature and not restrictive. Like reference numerals designate like elements throughout the specification.

Figure 2:
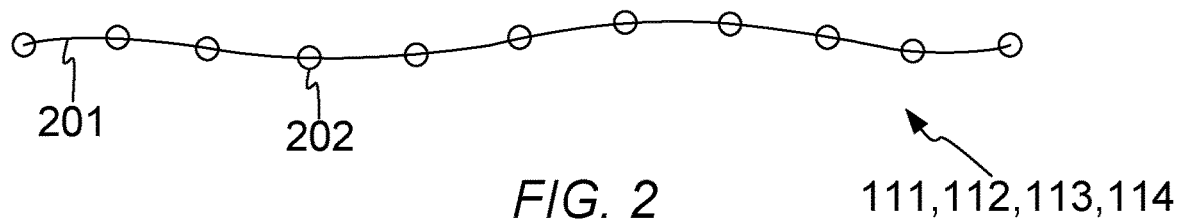
FIG. 2 illustrates a detector assembly of the device shown in FIG. 1, according to an embodiment of the present invention.

Referring now to FIGS. 1 and 2, a device for measuring radiation dosage is illustrated according to an embodiment of the present invention. The device 100 comprises a flexible sheet 110, on which is disposed one or more detector assemblies 111, 112, 113, 114. In the present embodiment four detector assemblies 111, 112, 113, 114 are illustrated, but in other embodiments the device 100 may comprise a different number of detector assemblies. The device 100 further comprises detector retaining means 120 for retaining the detector assemblies 111, 112, 113, 114 on the sheet 110 such that the detector assemblies 111, 112, 113, 114 will adopt the same curvature as the sheet 110 when the sheet no is deformed.

As shown in FIG. 2, each detector assembly 111, 112, 113, 114 comprises a plurality of beads 202 threaded onto a fibre 201. The plurality of beads 202 comprise radiation-sensitive material for recording information about a radiation dosage to which each bead 202 is exposed. In the present embodiment the beads 202 are spherical, although in other embodiments other shapes of bead could be used. Each bead 202 comprises a through-hole to allow the bead 202 to be threaded onto the fibre 201.

In the present embodiment the beads 202 are formed from silica glass, which is a thermo-luminescent material. Information about a radiation dosage experienced by a bead can be obtained using thermo-luminescence, by heating the bead to a sufficiently high temperature to cause the material of the bead to thermos-luminesce and radiate light. The intensity of the light produced by the bead depends upon the level of radiation that was received by the bead. In other embodiments optically-stimulated luminescence may be used to measure the radiation dosage experienced by each bead, instead of using thermos-luminescence. As a further alternative, in some embodiments an electron paramagnetic/spin resonance spectroscopy (EPR/ESR) system can be used to detect the number of trapped electrons in a bead, which is represented as an EPR/ESR signal. EPR or ESR constitutes a repeatable, non-destructive method of measuring the radiation dosage received by each bead. Furthermore, since EPR or ESR does not destroy the data stored within each bead, in the form of excited electrons, in embodiments in which EPR or ESR is used to give a measure of the radiation dosage the beads can be stored as a long-term record of the radiation dosage, providing a physical archive of patient data.

The fibre 201 may be a high-temperature resistant fibre. The fibre 201 may be formed from a material capable of withstanding the temperature required to cause thermo-luminescence of the material from which the beads 202 are formed. In some embodiments, the high-temperature resistant fibre 201 may be configured to withstand temperatures of at least 700 degrees Celsius. For example, the high-temperature resistant fibre 201 may be spun Kevlar, Nomex, silicon fibreglass, or ceramic fabric reinforced with glass. The high-temperature resistant fibre 201 may be a metallic wire. Using a high-temperature resistant fibre 201 may also allow the detector assembly 111, 112, 113, 114 to be sterilised using heat sterilisation.

An example of a reader apparatus suitable for reading the information recorded in the beads 202, so as to determine the radiation dosage to which each bead 202 was exposed, is disclosed in WO 2017/033029 A1. A detailed explanation of the operation of the reader will not be provided here, so as to avoid obscuring the present inventive concept. In brief, a detector assembly 111, 112, 113, 114 can be loaded into the reader while the beads 202 are still threaded onto the fibre 201. The detector retaining means 120 is configured to permit each detector assembly 111, 112, 113, 114 to be detached from the sheet 110 without removing the plurality of beads 202 from the fibre 201, so that the detector assembly 111, 112, 113, 114 can be loaded into the reader.

The reader can comprise a bead separation mechanism configured to slide an individual bead 202 along the fibre 201 so as to separate it from the other beads in the detector assembly 111, 112, 113, 114, and bead heating means for heating the separated bead 202 to cause it to thermo-luminesce. The reader may comprise a suitable light detector to measure the light produced by the bead 202 as it luminesces, and may further comprise a processor configured to convert the measured light intensity into a radiation dosage, which provides a measure of the radiation dosage to which that particular bead 202 was exposed.

Although in the present embodiment the beads 202 are formed of silica glass, in other embodiments different materials may be used for the beads 202. For example, the beads 202 may be formed of diamond, transparent carbon nanotubes, or high-temperature resistant thermo-luminescent polymers, such that they lose little data prior to heating in a reader. Alternatively the beads 202 may be made of optically stimulated luminescence materials, such as aluminium oxide, to prevent data loss before being exposed to optical stimulation in a reader. When optical stimulation is used, instead of the bead heating means the reader may comprise a light source for optically stimulating the beads to trigger luminescence.

By providing detector retaining means 120 on a flexible sheet 110, the detector assemblies 111, 112, 113, 114 can be made to adopt the same curvature as the sheet 110 when the sheet 110 is deformed. As a result, when the sheet 110 is placed against an object so as to adapt to the shape of the object, the detector assemblies 111, 112, 113, 114 can be used to capture information about radiation dosages at a plurality of points distributed over the surface of the object. This can be particularly advantageous when it comes to validating a beam configuration during radiotherapy, to confirm that the beam shape correctly conforms to the shape of the tumour to be treated. The information about the radiation dosage recorded in the dosimeter can also be used to confirm that healthy organs adjacent to the tumour, such as the rectum and bladder, have not been exposed to potentially harmful levels of radiation during the treatment.

In some embodiments, the plurality of beads 202 of the one or more detector assemblies 111, 112, 113, 114 may be distributed across a two-dimensional area of the sheet, such that when the sheet is deformed said plurality of beads provide a plurality of measurement points within a three-dimensional volume. Here, 'deformed' means that the surface of the sheet 110 is warped, for example as a result of the sheet 110 being folded or twisted. In other embodiments the sheet 110 may be formed from a stiff, flat sheet of material, such that the detector assemblies 111, 112, 113, 114 provide a two-dimensional array of radiation measurement points. Such arrangements can allow the variation in radiation dosage to be measured across two or three dimensions, in contrast to conventional linear dosimeters which can only measure radiation dosages along one axis.

The detector retaining means 120 may also be referred to as a detector retaining mechanism. The detector retaining means 120 can be embodied as any suitable coupling mechanism for temporarily coupling the detector assemblies 111, 112, 113, 114 to the sheet 110 in such a way that the detector assemblies 111, 112, 113, 114 can subsequently be detached from the sheet 110 without having to remove the plurality of beads 202 from the fibre 201.

By allowing each detector assembly 111, 112, 113, 114 to be detached from the sheet 110 while keeping the beads 202 on the fibre 201, the order of the beads can be preserved when the detector assembly 111, 112, 113, 114 is loaded into the reader. This allows the radiation dosage measurement obtained from each bead 202 to be related to a known position of that bead 202 on the sheet 110 while the device 100 was exposed to radiation, so as to determine a pattern of the radiation distribution in three dimensions. The positions of the beads can be recorded by capturing an image of the device 100, as will be described in more detail later.

Depending on the embodiment, different mechanisms may be used for the detector retaining means 120. In the present embodiment the detector retaining means 120 comprises a plurality of loops 120 of elastic material, for example rubber or plastic, through which the detector assemblies 111, 112, 113, 114 can be threaded. The loops 120 may be integrally formed as part of the sheet 110, or may be formed separately and subsequently affixed to the sheet 110. In other embodiments a removable fastening mechanism may be used, such as hook-and-loop fasteners. As yet a further alternative, in some embodiments an adhesive may be used to temporarily glue the detector assemblies 111, 112, 113, 114 to the sheet 110, and the detector assemblies 111, 112, 113, 114 may be subsequently separated from the sheet 110 by using a suitable solvent to dissolve the adhesive.

In some embodiments the sheet may comprise a biocompatible material, to permit the device 100 to be disposed in or on a human or animal body. This can allow radiation dosages to be measured in medical applications. The detector retaining means 120 may be configured so as to ensure that the detector assemblies 111, 112, 113, 114 will still be retained on the sheet 110 when the device is positioned in or on a human or animal body. That is, the detector retaining means 120 can be configured so as to withstand conditions to which the device 100 may be subjected to within a human or animal body, for example the range of pH conditions and temperatures that would be expected to occur within a human or animal body.

In some embodiments, at least one of the one or more detector assemblies 111, 112, 113, 114 may include one or more marker beads among the plurality of beads. The one or more marker beads are configured to be distinguishable from other ones of the plurality of beads in an image of the device 100, so that the position of the marker bead in the image can be easily determined. Different types of marker beads may be used, depending on the type of imaging technique that will be used to capture the image of the device 100. For example, the marker beads may be configured to be distinguishable from other ones of the plurality of beads in a Magnetic Resonance Imaging (MRI) image, an ultrasound image, an x-ray image, or a Computerised Tomography (CT) image.

Figure 3:
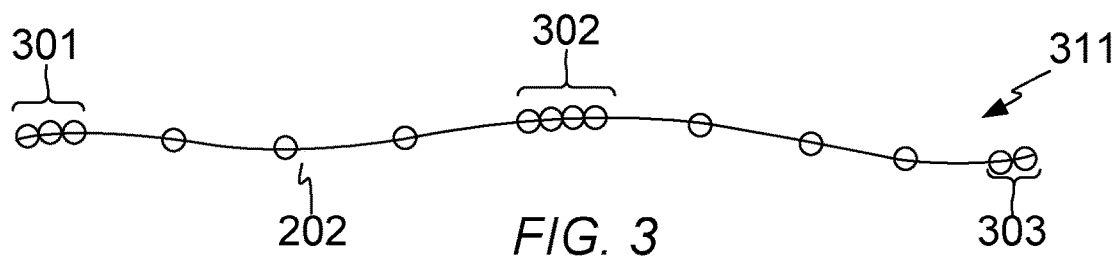
FIG. 3 illustrates a detector assembly comprising a plurality of clusters of marker beads, according to an embodiment of the present invention.

Once the position of the marker bead is known the positions of the remaining beads in the image can be determined, since the order of beads 202 along the fibre 201 is preserved when the detector assembly is removed from the sheet 110. Examples of different types of marker beads will now be described with reference to FIGS. 3 to 5. Referring to FIG. 3, a detector assembly comprising a plurality of marker beads is illustrated, according to an embodiment of the present invention. In the present embodiment the detector assembly 311 comprises a total of nine marker beads arranged into three separate clusters 301, 302, 303 along the fibre, but in other embodiments a different number of marker beads may be used. Each cluster 301, 302, 303 comprises a group of beads with a different inter-bead spacing to other ones of the plurality of beads along the fibre. In some embodiments each cluster 301, 302, 303 may include a different number of beads to other ones of the clusters 301, 302, 303 so as to allow a particular cluster to be uniquely identified in the image. For example, in the embodiment shown in FIG. 3 a first cluster 301 includes three beads, a second cluster 302 includes four beads, and a third cluster 303 includes two beads. It will be appreciated that these numbers are merely provided by way of example, and in other embodiments different numbers of clusters, and different numbers of beads within a cluster, may be used.

In embodiments in which the beads are able to slide freely along the fibre, each marker bead cluster may be held in place by the detector retaining means. For example, in the embodiment shown in FIG. 1, a marker bead cluster may be formed by positioning a certain number of beads between a pair of elastic loops 120, one loop being disposed at either end of the cluster so as to prevent the beads within the cluster sliding along the fibre. In other embodiments a separate mechanism may be used to keep the marker beads in place within a cluster, for example the marker beads may be held within a tight-fitting tube, sleeve or tape which is separate from the detector retaining means.

Figure 4:
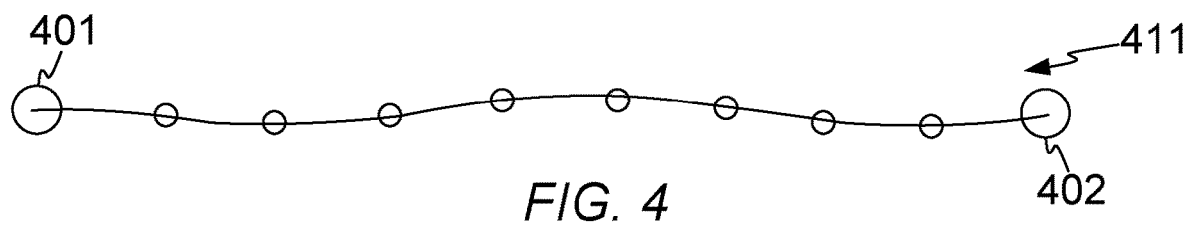
FIG. 4 illustrates a detector assembly comprising a plurality of marker beads having different sizes to the other beads, according to an embodiment of the present invention.

Referring now to FIG. 4, a detector assembly 411 is illustrated which comprises a plurality of marker beads 401, 402 having different sizes to other ones of the plurality of beads. In the present embodiment the marker beads 401, 402 have a larger diameter than the other beads in the detector assembly 411. In other embodiments the marker beads may have a different shape to the other beads in the detector assembly, instead of or in addition to having a different size. By using a bead of a different shape and/or size as a marker bead, the marker bead can easily be distinguished from other ones of the beads in the image of the device.

Figure 5:
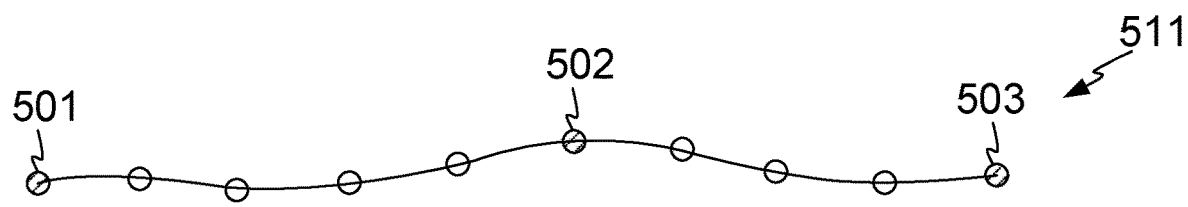
FIG. 5 illustrates a detector assembly comprising a plurality of marker beads formed of different material to the other beads, according to an embodiment of the present invention.

Referring now to FIG. 5, a detector assembly 511 is illustrated in which a plurality of marker beads 501, 502, 503 are formed of different material to the other ones of the plurality of beads, according to an embodiment of the present invention. The material of the marker beads can be selected so as to provide contrast with the other beads in the image. For example, in a detector assembly 511 configured for use with MRI imaging, the marker beads may be formed of titanium and the other beads may be formed of silica glass. Titanium will appear brighter than silica glass in the MRI image, allowing the marker beads to be easily distinguished. As a further example, in a detector assembly 511 configured for use with CT imaging, the marker beads may be formed of stainless steel or any other biocompatible metal, such as aluminium, platinum or gold, while the other beads may be formed from silica glass.

Figure 6:
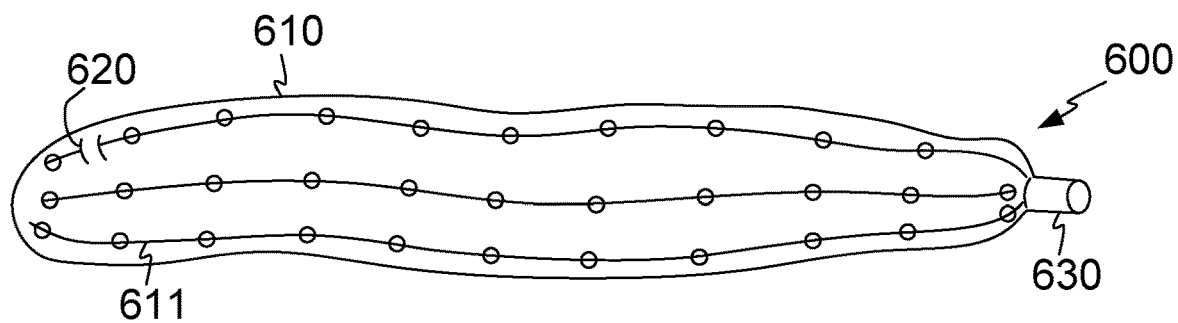
FIG. 6 illustrates a device for measuring radiation dosage according to an embodiment of the present invention, the device comprising a plurality of detector assemblies disposed on the surface of an inflatable balloon.

In some embodiments of the invention, the sheet on which the one or more detector assemblies are disposed may form the wall of an inflatable balloon, as shown in FIG. 6. In this embodiment, the device 600 comprises a balloon 610 having an outer wall formed from a flexible sheet material. The balloon 610 comprises a fluid inlet 630 adapted for connection to a source of fluid for inflating the balloon 610. For example, the fluid may be saline solution. The sheet from which the wall of the balloon 610 is formed may comprise an impermeable membrane, such that when fluid is pumped into the balloon through the fluid inlet 630 the fluid is retained within the balloon 610, thereby increasing the fluid pressure within the balloon 610 and causing the balloon 610 to expand. Depending on the embodiment, the one or more detector assemblies 611 may be disposed on an inner surface and/or an outer surface of the balloon 610.

The device 600 may be inserted into a void, for example a body orifice or cavity, and then the balloon 610 can be inflated to force the detector assemblies 611 against a wall of the void. In this way, the detector assemblies 611 will adopt the shape of the void, and can be used to measure the radiation dosage at various points around the surface of the void.

Three detector assemblies 611 are illustrated in FIG. 6, but it will be appreciated that different numbers of detector assemblies may be provided in other embodiments. Furthermore, although only one side of the balloon 610 is illustrated in FIG. 6, it will be appreciated that additional detector assemblies 611 may be disposed on a rear side of the balloon 610. As with the embodiment of FIG. 1, in the embodiment of FIG. 6 the wall of the balloon 610 includes detector retaining means in the form of elastic loops 620 through which the detector assembly 611 can be threaded.

Figure 7:
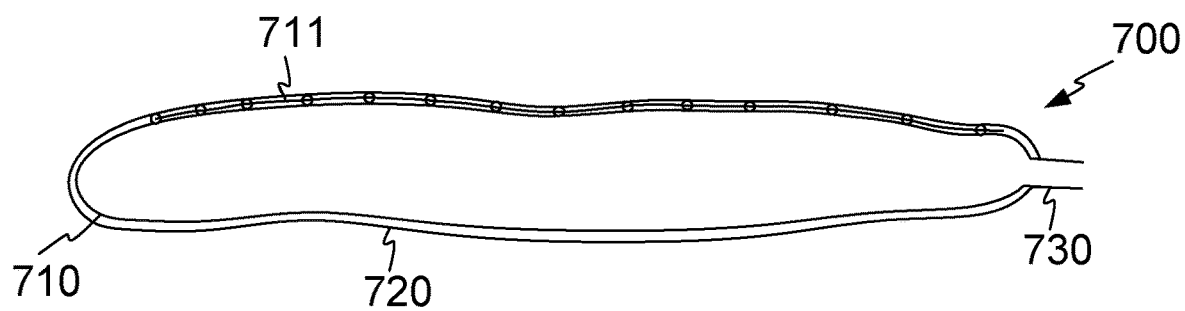
FIG. 7 illustrates a cross-sectional view of a device for measuring radiation dosage comprising a detector assembly sandwiched between two balloons, according to an embodiment of the present invention.

Referring now to FIG. 7, a device for measuring radiation dosage is illustrated in cross-section, according to an embodiment of the invention. The device 700 of the present embodiment is similar to the device of 600 in that it comprises an inflatable balloon 710, a fluid inlet 630 for connection to a source of fluid for inflating the balloon 710, and one or more detector assemblies 711 disposed on a surface of the balloon.

The device 700 of the present embodiment comprises detector retaining means in the form of a second layer of sheet material 720 disposed around the one or more detector assemblies 711 and the balloon 710. The second layer of sheet material 720 extends around a circumference of the balloon 710. In the present embodiment the second layer of sheet material 720 is in the form of a second balloon with encloses the first balloon. In other embodiments, the second layer of sheet material 720 may comprise a band of material surrounding part of the balloon 710.

The second layer of sheet material 720 is sized such that when the balloon 710 is inflated, the one or more detector assemblies 711 are tightly held between the second layer of sheet material 720 and the wall of the balloon 710. For example, the second layer of sheet material 720 may have a similar size to the balloon 710. In this way, the one or more detector assemblies 711 are sandwiched between the balloon 710 and the second layer of sheet material 720, and can be prevented from moving within the space between the balloon 710 and the second layer of sheet material 720. The second sheet material 720 may be formed from an impermeable membrane similar to the wall of the balloon 710. Alternatively, the second sheet material 720 may be permeable. In some embodiments the second sheet material 720 may comprise an open mesh, for example a woven material.

Figure 8:
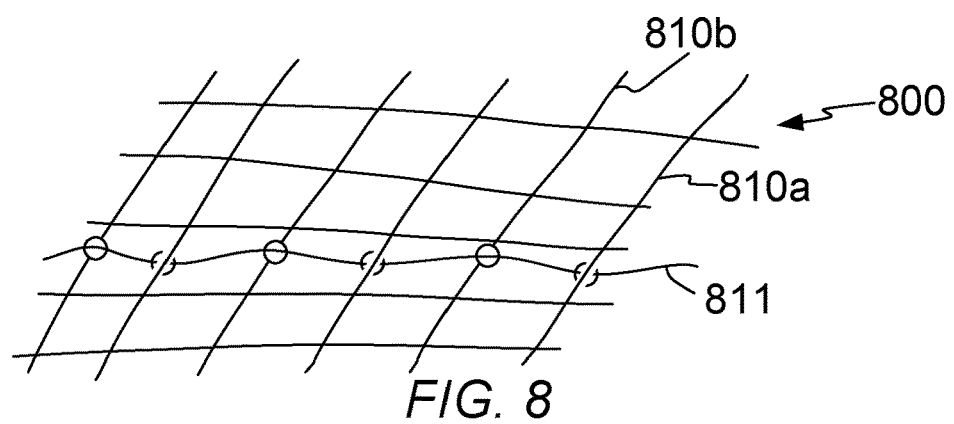
FIG. 8 illustrates a device for measuring radiation dosage comprising a sheet of open mesh material, according to an embodiment of the present invention.

Referring now to FIG. 8, a device for measuring radiation dosage is illustrated according to an embodiment of the present invention. In this embodiment the device 800 comprises a sheet of open mesh material, for example a textile material. As used herein, the term 'mesh' can also encompass non-woven materials, for example a continuous sheet of material with multiple openings formed through the sheet.

In the present embodiment the open mesh comprises a plurality of interwoven fibres 810a, 810b. In this embodiment, fibres 810a, 810b that are integral to the mesh act as the detector retaining means, with the one or more detector assemblies 811 being woven between said fibres as shown in FIG. 8.

Figure 9:
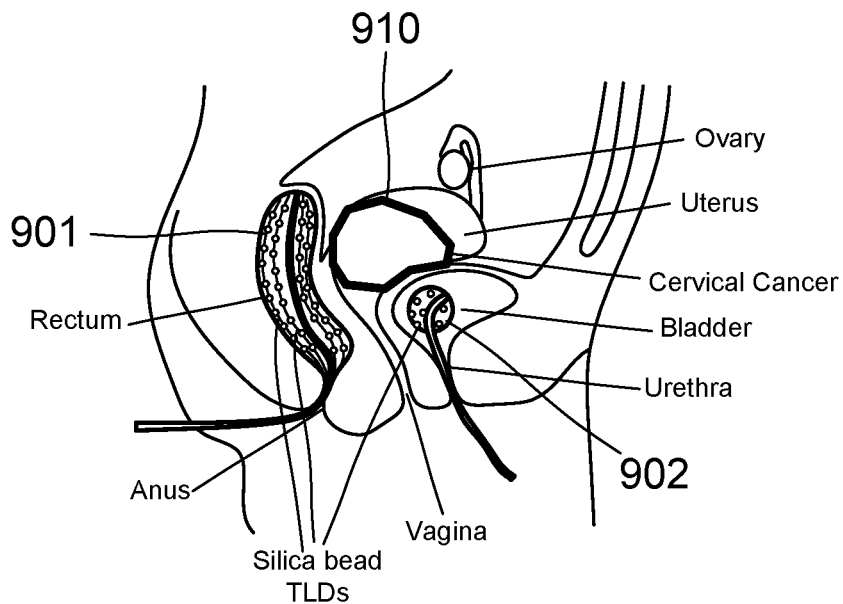
FIG. 9 illustrates devices for measuring radiation dosages in a female human subject, according to embodiments of the present invention.
Figure 10:
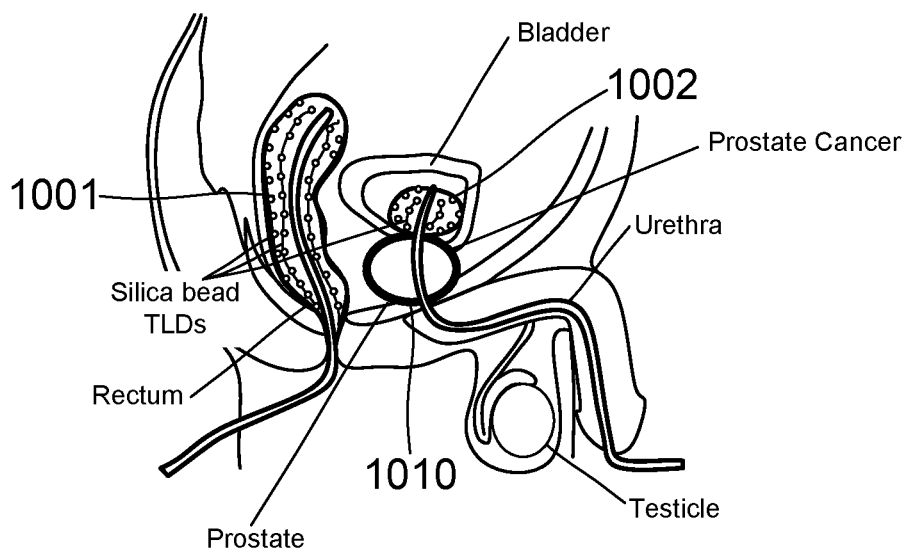
FIG. 10 illustrates devices for measuring radiation dosages in a male human subject, according to embodiments of the present invention.

Referring now to FIGS. 9 and 10, embodiments of the present invention are illustrated in which devices for measuring radiation dosages are provided in the form of inflatable balloons, similar to those shown in FIGS. 6 and 7, and adapted for insertion into a body cavity or organ of a human or animal body. FIG. 9 illustrates devices 901 and 902 for measuring radiation dosages in a female human subject, according to embodiments of the present invention. In FIG. 9, a first device 901 comprises sheet material in the form of a balloon adapted for insertion into a rectal cavity, and a second device 902 comprises sheet material in the form of a balloon adapted for insertion into the bladder via the urethra. One or both devices 901, 902 may be used to measure the radiation dosage when treating a tumour 910, since when inflated in the rectal cavity or in the bladder the detector assemblies in the devices 901, 902 will be pressed against the tumour 910. FIG. 10 illustrates similar devices 1001, 1002 for measuring radiation dosages in a male human subject when treating a prostate tumour 1010.

Figure 11:
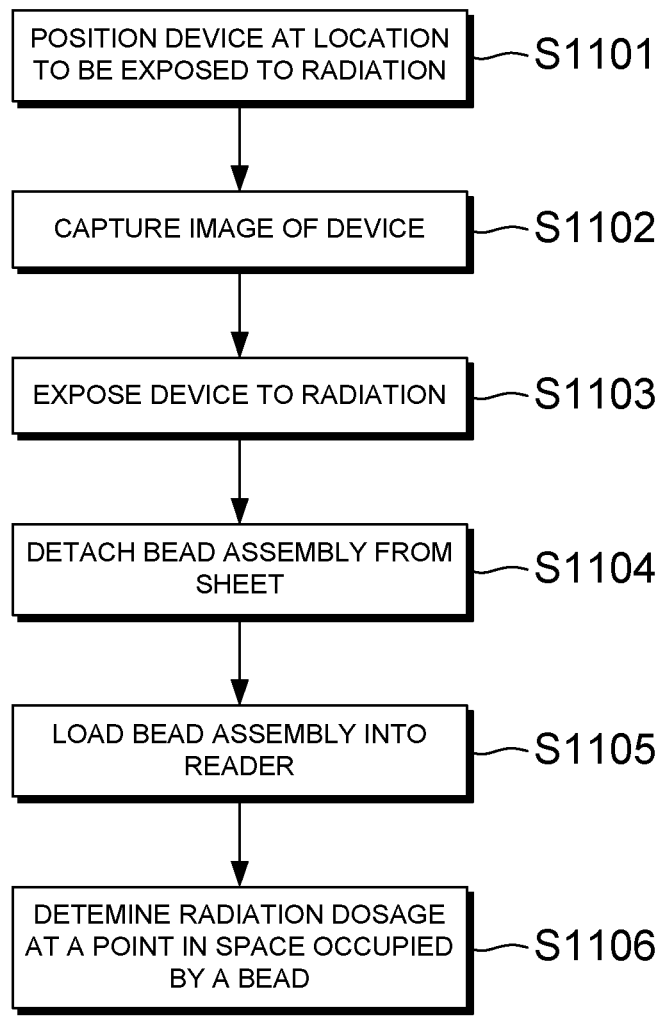
FIG. 11 is a flowchart showing a method of detecting a radiation dosage, according to an embodiment of the present invention.

Referring now to FIG. 11, a flowchart showing a method of detecting a radiation dosage is illustrated, according to an embodiment of the present invention. The method can be used with any of the devices disclosed herein. First, in step S1101 the device is positioned at a location to be exposed to radiation, and then the device is exposed to radiation in step S1102.

Next, in step S1103 an image is captured of the device in-situ, that is to say, at the location in which it has been exposed to radiation. Although in the present embodiment the image is captured after the device is exposed to the radiation, in general the image may be captured before, during or after the device is exposed to the radiation.

Next, one of the one or more detector assemblies is detached from the sheet in step S1104, and loaded into the reader in step S1105. Then, in step S1106 the radiation dosage at a point in space is determined based on the radiation dosage read from one of the plurality of beads, and the position of said one of the plurality of beads in the captured image. That is, by comparing the radiation dosage read from a particular bead to the location of that bead in the captured image, the radiation measurement from the bead can be assigned to the point in space occupied by that bead while the device was exposed to radiation. In this way, a two-dimensional or three-dimensional map of the radiation intensity across the device can be constructed.

Figure 12:
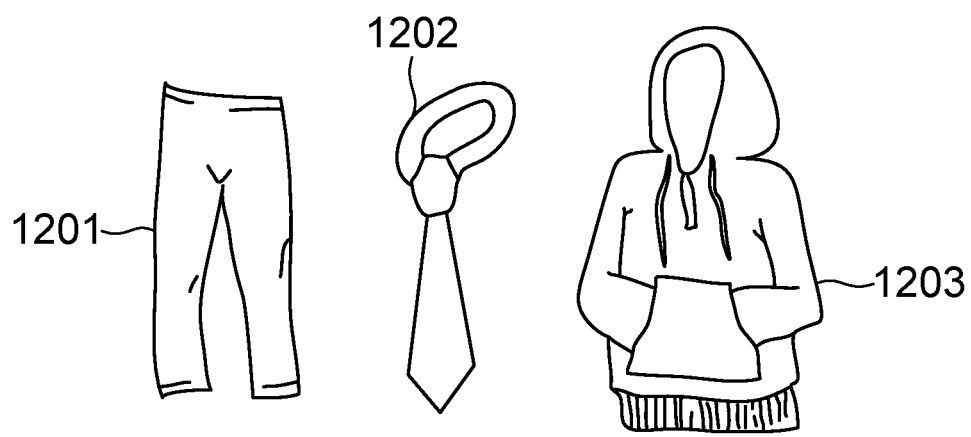
FIG. 12 illustrates a plurality of wearable items incorporating devices for measuring a radiation dosage, according to embodiments of the present invention.

Embodiments of the present invention have been described in relation to devices for measuring a radiation dosage, particularly in the context of medical applications such as radiotherapy. However, embodiments of the present invention are not limited to medical applications. In some embodiments the device may be incorporated into a part or whole of a wearable item 1201, 1202, 1203, as shown in FIG. 12. Such embodiments can allow measurements of radiation dosage in other contexts, for example to monitor occupational exposure of workers to radiation. For example, a device such as the one shown in FIG. 8 may be woven into the fabric of items of clothing such as the ones shown in FIG. 12.

Whilst certain embodiments of the invention have been described herein with reference to the drawings, it will be understood that many variations and modifications will be possible without departing from the scope of the invention as defined in the accompanying claims.

The invention claimed is:

1. A device for measuring radiation dosage, the device comprising:
   a sheet;
   one or more detector assemblies disposed on the sheet, each said one or more detector assemblies comprising a plurality of beads threaded onto a fibre, the plurality of beads comprising radiation-sensitive material for recording information about a radiation dosage to which each said bead is exposed; and
   detector retaining means for retaining the one or more detector assemblies on the sheet, the detector retaining means being configured to permit said each one or more detector assemblies to be subsequently detached from the sheet without removing the plurality of beads from the fibre.

2. The device according to claim 1, wherein the sheet is configured to be flexible and the plurality of beads of the one or more detector assemblies are distributed across a two-dimensional area of the sheet, such that when the sheet is deformed the plurality of beads provide a plurality of radiation measurement points within a three-dimensional volume.

3. The device according to claim 2, wherein at least one of the one or more detector assemblies includes one or more marker beads among the plurality of beads, the one or more marker beads being configured to be distinguishable from other ones of the plurality of beads in an image of the device.

4. The device according to claim 1, wherein at least one of the one or more detector assemblies includes one or more marker beads among the plurality of beads, the one or more marker beads being configured to be distinguishable from other ones of the plurality of beads in an image of the device.

5. The device according to claim 4, wherein the one or more marker beads are formed of different material to the other ones of the plurality of beads so as to provide contrast with said other ones of the plurality of beads in the image.

6. The device according to claim 4, wherein the one or more marker beads have a different shape and/or size to said other ones of the plurality of beads.

7. The device according to claim 4, wherein the one or more marker beads comprise a cluster of beads with a different spacing between beads along the fibre, relative to a spacing between said other ones of the plurality of beads along the fibre.

8. The device according to claim 4, wherein the one or more marker beads are configured to be distinguishable from other ones of the plurality of beads in one or more of a Magnetic Resonance Imaging MRI image, an ultrasound image, an x-ray image, or a Computerised Tomography CT image.

9. The device according to claim 8, wherein the one or more marker beads are formed of different material to the other ones of the plurality of beads so as to provide contrast with said other ones of the plurality of beads in the image.

10. The device according to claim 1, wherein the sheet forms a wall of an inflatable balloon, the balloon comprising a fluid inlet adapted for connection to a source of fluid for inflating the balloon.

11. The device of claim 10, wherein the detector retaining means comprises a second layer of sheet material disposed around the one or more detector assemblies and the balloon, the second layer of sheet material extending around a circumference of the balloon and being sized such that the one or more detector assemblies are tightly held between the second layer of sheet material and the wall of the balloon when the balloon is inflated.

12. The device of claim 11, wherein the second layer of sheet material is in the form of a second balloon.

13. The device of claim 10, wherein the balloon is adapted for insertion into a body cavity or organ of a human or animal body.

14. The device of claim 13, wherein the body cavity is a rectal, oral or vaginal cavity, or wherein the organ is a bladder.

15. The device of claim 1, wherein the sheet comprises an open mesh.

16. The device of claim 15, wherein the detector retaining means comprises second fibres integral to the mesh, the one or more detector assemblies being woven between said second fibres.

17. The device of claim 1, wherein the sheet comprises a part or whole of a wearable item.

18. The device according to claim 1, wherein the sheet comprises a biocompatible material.

19. The device according to claim 18, wherein the detector retaining means is configured to retain the one or more detector assemblies on the sheet when the device is positioned in or on a human or animal body.

20. A method of detecting radiation dosage using a device according to any one of the preceding claims, the method comprising:

positioning the device at a location to be exposed to radiation;
exposing the device to radiation;
capturing an image of the device at said location, before, during or after the device is exposed to the radiation;
detaching one of the one or more detector assemblies from the sheet;
loading said one of the one or more detector assemblies into a reader for reading a radiation dosage recorded by each of the plurality of beads; and
determining a radiation dosage at a point in space based on the radiation dosage read from one of the plurality of beads and a position of said one of the plurality of beads in the captured image.

* * * * *